(12) United States Patent
Mack et al.

(10) Patent No.: US 8,626,523 B1
(45) Date of Patent: Jan. 7, 2014

(54) PATIENT VOICE CHECK-IN SYSTEM

(75) Inventors: Joseph A. Mack, Worthington, OH (US); Nicholas P. Nelson, New Albany, OH (US)

(73) Assignee: MedOne Systems, LLC, New Albany, OH (US)

( * ) Notice: Subject to any disclaimer, the term of this patent is extended or adjusted under 35 U.S.C. 154(b) by 1937 days.

(21) Appl. No.: 11/104,386

(22) Filed: Apr. 12, 2005

(51) Int. Cl.
  *G06Q 50/00* (2012.01)
(52) U.S. Cl.
  USPC .............................................. 705/2
(58) Field of Classification Search
  USPC .................................... 705/2, 3, 4
  See application file for complete search history.

(56) References Cited

U.S. PATENT DOCUMENTS

| | | | |
|---|---|---|---|
| 5,878,403 A | 3/1999 | DeFrancesco et al. | 705/38 |
| 6,014,645 A | 1/2000 | Cunningham | 705/38 |
| 7,092,496 B1 * | 8/2006 | Maes et al. | 379/88.01 |
| 7,213,742 B1 * | 5/2007 | Birch et al. | 235/375 |
| 7,280,975 B1 * | 10/2007 | Donner | 705/10 |
| 7,756,723 B2 * | 7/2010 | Rosow et al. | 705/2 |
| 2003/0220817 A1 * | 11/2003 | Larsen et al. | 705/2 |
| 2004/0153337 A1 * | 8/2004 | Cruze | 705/2 |
| 2005/0108057 A1 * | 5/2005 | Cohen et al. | 705/3 |
| 2005/0251417 A1 * | 11/2005 | Malhotra et al. | 705/2 |
| 2006/0004605 A1 * | 1/2006 | Donoghue et al. | 705/2 |
| 2006/0155578 A1 * | 7/2006 | Eisenberger et al. | 705/2 |
| 2007/0073555 A1 * | 3/2007 | Buist | 705/2 |

* cited by examiner

*Primary Examiner* — John Pauls
(74) *Attorney, Agent, or Firm* — Standley Law Group LLP

(57) ABSTRACT

A system for obtaining patient medical information from a currently treating physician to a hospital admitting physician. A physician wishing to admit a patient dials a phone number, enters relevant patient medical data, and then leaves a recording describing the patient's condition. This recording is then stored in a database where it can be played back through an electronic medical record. The recording is also sent directly to the admitting physician's cell phone who can then tend to the patient as needed.

9 Claims, 3 Drawing Sheets

PATIENT VOICE CHECK-IN SYSTEM

The present invention relates generally to a system and method for checking a patient into a hospital. More particularly, the present invention relates to a method and system for checking a patient into a hospital group via a voice check-in system.

BACKGROUND AND SUMMARY OF THE INVENTION

Doctors that need to admit a patient to an inpatient physician currently face a complicated process of trying to figure out which physician to call. They have to determine which physician group to admit the patient to, then check that group's call schedule and page the admitting doctor. If the emergency room doctor is lucky enough to have called the proper pager number, the admitting doctor typically returns the page in 10-30 minutes. By this time, the emergency room doctor has seen several other patients and now has to answer the phone and refocus on the patient that they need to admit to the hospital. Often, the admitting physician isn't even the physician who ends up admitting the patient to the hospital due to the admitting group's logistical concerns. In this case, the admitting physician will check the patient out to one of their partners. Information is inevitably lost during this process as it goes from one physician's memory to another physician's memory.

The present invention recognizes the limitations of "pager tag" for both the referring physician (e.g., emergency room doctor) and admitting physician. The present invention uses programmed computer and telephony technology to streamline the process for all users. Once the referring physician recognizes that the patient needs to be admitted to a practice that utilizes this invention, they call a predetermined phone number, i.e., a "voice check-in" number, (doctors also refer to this process as a "check-out" procedure), enter relevant patient identification data, e.g., the patient's medical record number, then leave a voice recording detailing pertinent medical information regarding the patient. By calling the predetermined voice check-in number, the referring physician does not have to search for and identify the admitting physician or his or her unique phone or pager number. The phone system of the present invention receives and stores the patient identification data and recording into a computer database admission queue that can be accessed by the admitting and/or rounding physicians. The invention also checks an admitting physician call database so it can determine which physician is currently designated as the group's admitting physician, then it calls their cell phone and plays the recorded information so that the admitting physician can provide admitting orders and determine when the patient needs to be seen. The admitting physician may also assign the patient to another rounding physician in his or her practice group. In one embodiment, the recording is played at a faster rate so that the physician can listen to the recording quicker. Because the system of the present invention automatically identifies and calls the appropriate admitting doctor with the recorded check-in message, the referring doctor does not have to manually identify and page the admitting doctor. The referring doctor also does not have to wait to receive a call from the admitting physician. The referring doctor can rest assured that once the voice check-in message is left, that the system will take care of automatically getting the message to the appropriate admitting physician.

In another embodiment, the invention is comprised of a "family check-in" system where the doctor can leave daily check-ins through an electronic medical record and have family members retrieve the check-ins via a PIN that is assigned to the patient during the admission process. This will eliminate the need for doctors and family members to play phone tag.

Obvious modifications to the present invention are expected to fall within the scope of the claims of the present invention. The above stated and other advantages of the present invention will be better understood from the following description of the drawings and detailed description of the preferred embodiment(s).

BRIEF DESCRIPTION OF THE DRAWINGS

A better understanding of the present invention will be obtained when reference is made to the accompanying drawings, wherein.

DETAILED DESCRIPTION OF A PREFERRED EMBODIMENT

Figure 1:
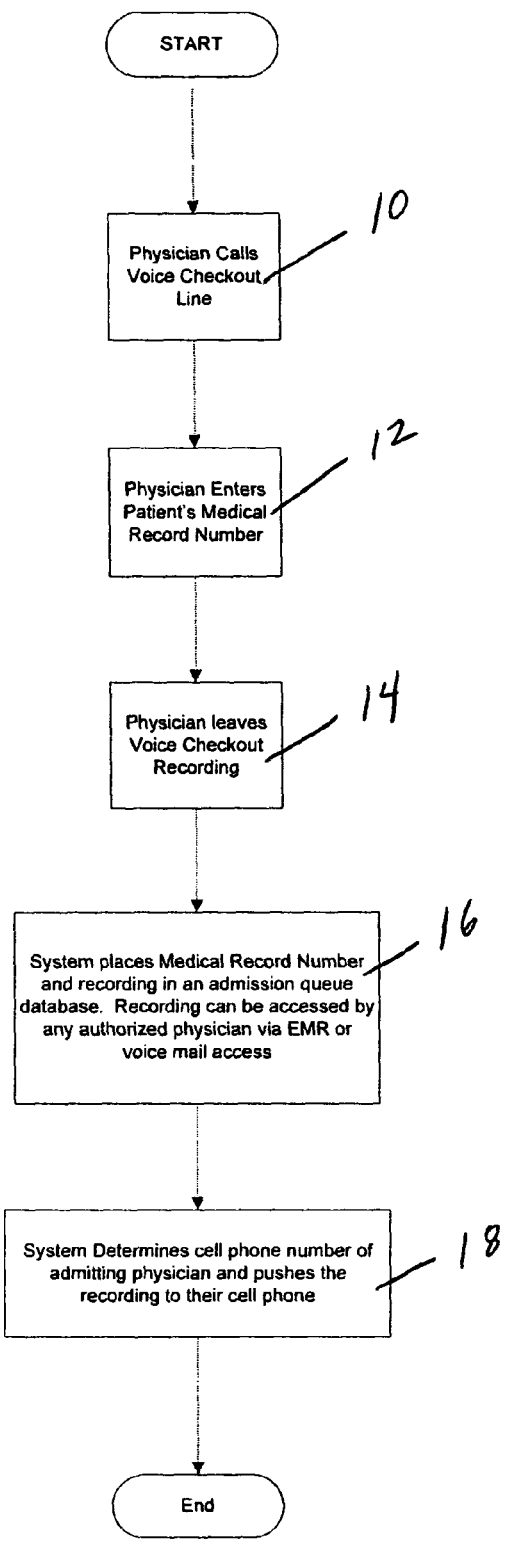
FIG. 1 is a flowchart depicting the steps of one embodiment of the present invention.

The present invention uses programmed computer and telephony technology to streamline the process of checking in patients to hospitals for all users. FIG. 1 is a flowchart depicting the steps of one embodiment of the present invention. Once the referring physician (e.g., emergency room physician) recognizes that the patient needs to be admitted to a practice that utilizes this invention, they call a predetermined "voice check-in" number 10 (doctors also refer to this process as a "check-out" procedure), enter relevant patient identification data, e.g., the patient's medical record number 12 (either through touch-tone or speak recognition), then leave a recording detailing pertinent medical information regarding the patient 14. The phone system places the patient identification data and recording into a computer database admission queue (for example, in a SQL server table) that can be accessed later by the admitting or rounding physicians 16. The recording can be accessed by any authorized physician via an EMR ("Electronic Medical Record") tool or voice mail access. The invention also checks the admitting physician call database so it can determine which physician is currently designated as the group's admitting physician. Once the admitting physician is identified, the system preferably calls the admitting physician's cell phone and plays the recorded information so that the admitting physician can provide admitting orders and determine when the patient needs to be seen 18. In one embodiment, the recording is played at a faster rate so that the physician can listen to the recording quicker. In the preferred embodiment, if the admitting physician does not answer his or her phone, the system is programmed to make additional call attempts (e.g., every 10 minutes) in an attempt to reach the physician.

Figure 2:
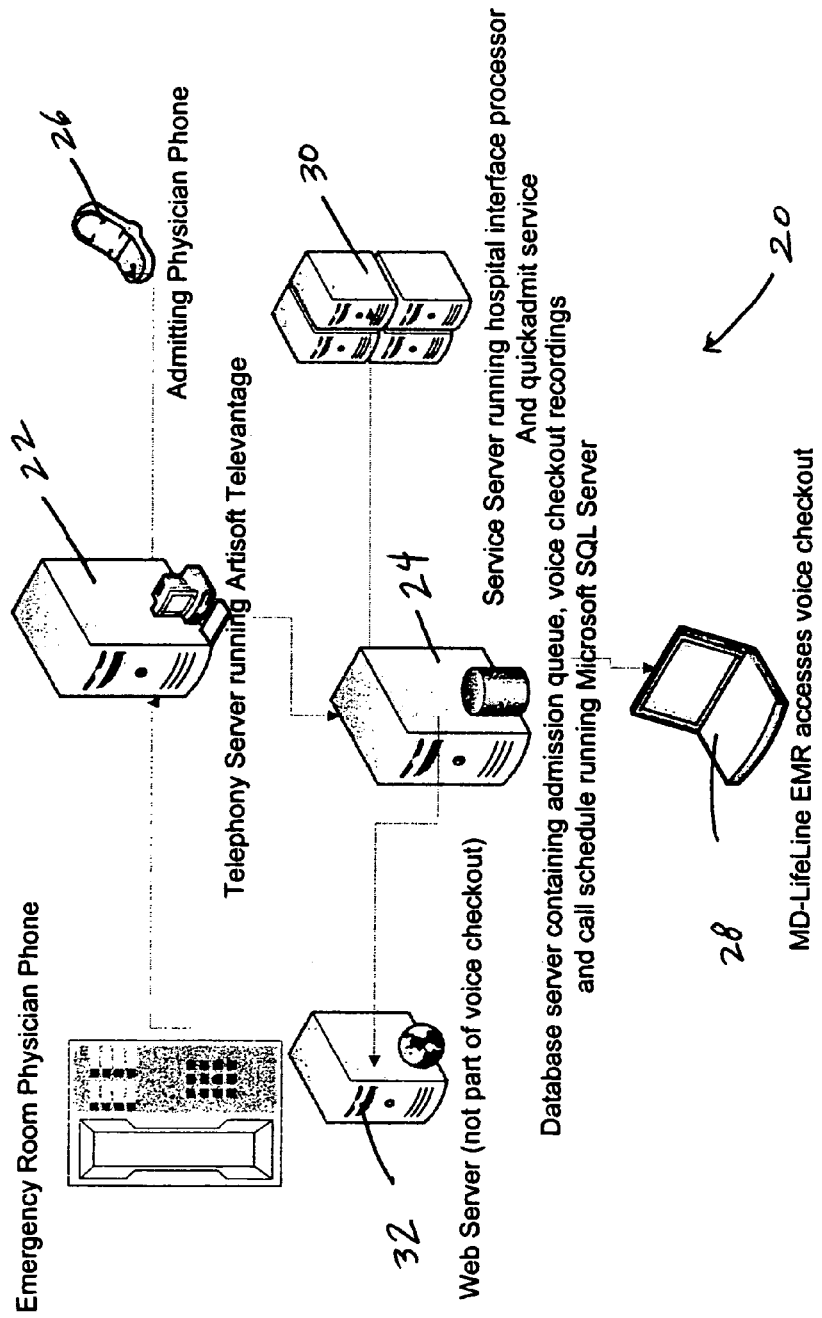
FIG. 2 is a block diagram of the components of one embodiment of the present invention.
Figure 3:
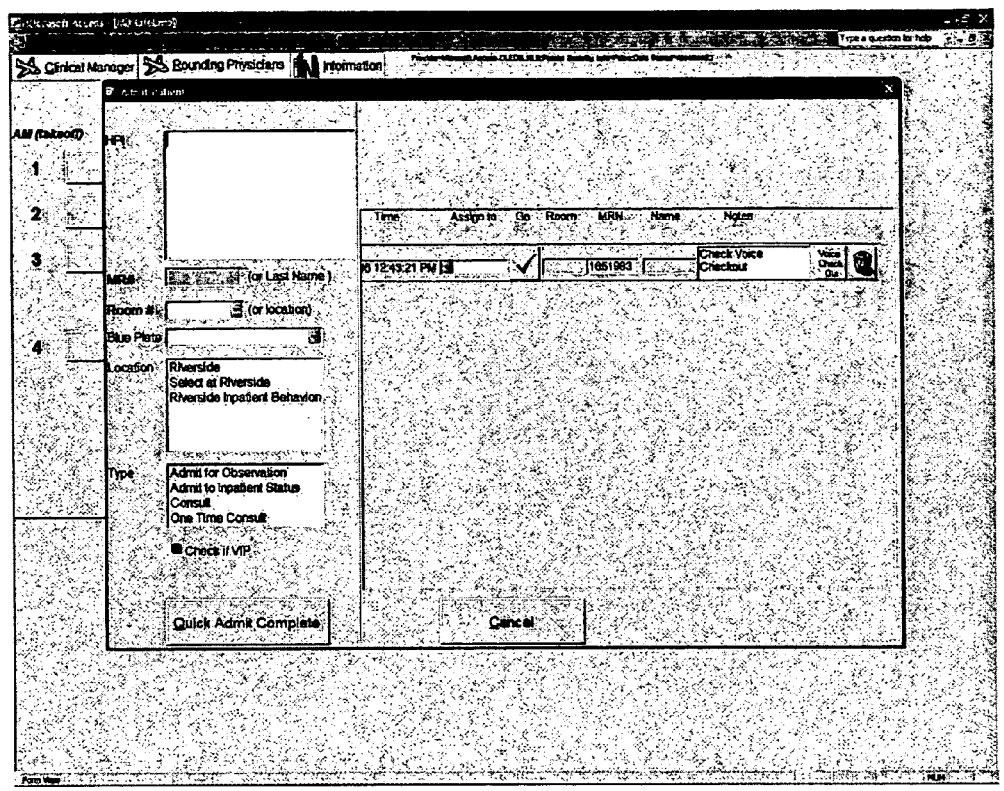
FIG. 3 illustrates a sample screen shot of an admission queue.

A first embodiment of the present invention 20 is illustrated in FIG. 2. In one embodiment, the invention is comprised of a telephone server or software module 22 for taking the referring physician's call, and receiving and storing the patient identification data and other patient information. The patient's identification data may be a medical record number or other unique identification such as social security number for example. The telephone servers sends the received data to the database server or data memory 24 where it is stored, preferably in an admission queue. FIG. 3 illustrates a sample screen shot of an admission queue. In the preferred embodiment, the database also contains the call (rounding) schedule for the hospital group. It is preferred that the call schedule indicate the admitting doctor's name and cell phone number. The system is programmed to automatically initiate a phone call to the mobile phone 26 of the admitting physician and to play the voice recording of the patient check-in to the admitting physician. The admitting physician can then tend to the patient as needed.

The admitting physician may assign the "checked-in" patient to another rounding physician, preferably through the mobile EMR tool 28. The EMR tool is a software application or module loaded on a mobile computing platform, such as a personal computer, that a rounding physician uses to access and update admission queues and patient records stored in the database server 24 and possibly other information stored in hospital records. The physician's mobile computing platform may connect to the system of the present invention via a wireless network or by synchronization stations found throughout the hospital. Upon being assigned a patient, the rounding physician may be sent an alert that a patient has been assigned to him or her (the alert can be in the form of a page, email, text message, flashing font or special color font, for example). The rounding physician can then use his or her EMR tool to view the admission queue and receive details of the assigned patient, including playing back the recorded voice message left by the referring physician.

In one embodiment, additional patient data can also be appended to the check-in data of the admitted patient. For example, once the check-in data for a patient is added to the admission queue, a Quickadmit service (preferably a program written in vb.net running on a server 30) scans the admission queue periodically (e.g., every 30 seconds) for check-ins that don't have patient demographics. For check-ins that do not have saved demographics, an automatic call is made to a lab request web service for the hospital over a secure Internet socket to request patient information, for example, patient demographics, the last 30 days of labs, the last 3 years of studies, and the current hospital medications. The service then looks for a response to the request, and once it receives a response, it marks the record as having received the patient information. The received information is then preferably stored in the database (preferably in a separate table) and linked to the client check-in file by the patient identification, e.g., medical record number. The rounding physicians can then receive the updated information via synchronization through their EMR tools, e.g., using SQL Server replication functionality over a secure Internet connection (which may be wired or wireless) to obtain the patient information before admitting the patient. If wireless, the system can be programmed to synchronize as soon as new data is received by the system and stored in the database. For example, the system can be sent to synchronize as soon as a new check-in file is received through the voice check-in procedure. In another example, the system can be sent to synchronize automatically when patient demographic is received from the hospital.

Accordingly, in one embodiment, a referring physician (e.g., emergency room doctor) will take the following steps to check a patient in:
1. Dial the predetermined phone number;
2. Enter the patient medical number by touch-tone or speech recognition;
3. Leave details of patient checking in via voice message, for example
   name;
   patient name;
   past medical history;
   medication list;
   allergies;
   reason for hospitalization;
   recent labs or studies;
   any other pertinent data;
   call back number;
   whether a consult with doctor is necessary.

The present invention can also be configured to service a system servicing multiple, distributed hospitals. In the case where the system services multiple hospital locations, it is preferred that the distributed locations be serviced by the same telephone server and database, although multiple server sites may be used. In one embodiment, one check-in phone number may be used for all the hospitals where the referring physician indicates to the system (e.g., by entering a hospital code or through menu selection) which hospital the patient is located. In another embodiment, a unique check-in phone number can be used for each respective hospital location where the telephone server is programmed to determine the appropriate hospital location based on the dialed number (e.g., using DNIS or DID signals). Once the system of the present invention determines which hospital the patient is located, the system can then store the patient data into the admission queue for that hospital, identify the admitting physician for that hospital from the rounding schedule for that hospital, and automatically call the admitting physician for that hospital with the recorded voice check-in message. Patient information can also be requested from each hospital and appended to the client files as previously discussed.

The following paragraphs provide additional detail on various components of the present invention:

Database Server

In one embodiment, the database server is a SQL server. This server preferably has redundant hard drives and is backed up every night. This is the system that the physician EMR tools connect to either inside the office or over a secure virtual private network via the Internet to synchronize their local database copies. It also may run other nightly jobs such as generate daily encounters and billing jobs.

Web Server

In one embodiment, the web server 32 serves several web sites on the Internet. First, it hosts the interface web service. This may be a vb.net web service that "catches" XML based lab/demographic feeds from hospitals. In the preferred embodiment, this service catches the feeds and stores the data into the SQL database, another service actually processes them (discussed later). It can also host the calls web site (a way for physicians to change how their calls are routed in case they have a meeting or some other event where they do not want to be interrupted). It may also host a mobile version of the calls site so that they can change the calls through their cell phone browser. It may also host the consult site, where unit clerks can enter consults. The web server also hosts other notification web sites for nightly history and physicals (H&Ps), central lines, critical care, and death pronouncement notifications, as well as our admit report, which allows physicians to view the H&Ps for patients processed the night before.

Telephony Server

The telephony server in one embodiment is an Artisoft Televantage Server. This system runs a Windows based PBX. It can be programmed with custom developed integrated voice response (IVR) scripts. For example, in one embodiment, the IVR can be programmed with a voice check-in script, phone routing software, H&P check-in application, admit line round robin router, and external practice phone routing software (more details of these scripts are discussed below). It can also be configured to run a persistent pager service. In one embodiment it has a T1 card in it to connect to an ISDN PRI phone trunk line. It can also be configured with a digital phone card, as well as analog trunk board. The telephony server may also run its own version of SQL Server.

Service Server

In one embodiment, a service server is programmed to run several vb.net based windows services, including autofax service, autosynch service, labprocessor service, textpager service, and quickadmit service. It is also appreciated that the service server may be combined into the same hardware with one or more of the other servers disclosed in FIG. 2.

Nightly Autosynch Service

The nightly autosynch service automatically synchronizes any laptop plugged in to the internal network. In one embodiment, it runs at 12 a.m., 5 a.m., and 6 a.m. Automatically synchronizing the laptops at night reduces the risk of someone forgetting to synch at the end of the day. It also reduces the time required to synch in the morning before the start of daily rounds. In one embodiment, the program broadcasts an activation message for each laptop to turn them on, before starting the synchronization job. Once the job is finished, the laptops will go into standby mode.

QuickAdmit Service

In one embodiment, the QuickAdmit service vb.net program is programmed to periodically check for new patients in the admission queue table. If it sees a new patient, it sends a request securely over the Internet to the hospital lab system, requesting the last 30 days of labs and the last 3 years of studies, the current hospital medication list, and the patient's demographic information. It keeps requesting this information until it is received. It also scans for any H&P ("History and Physical") checkouts left though the H&P check-in IVR. It matches the social security number entered through the H&P check-in with any patient that shows up in the admission queue through the unit clerk web site. If it finds a match, it attaches the H&P checkout to the admission notification.

LabProcessor Service

In one embodiment, the LabProcesser program is a vb.net program that scans for unprocessed lab information sent over the Internet from the hospital. It processes any unprocessed information into a format readily digestible by the EMR tool used by the physicians.

Textpager Service

In one embodiment, the Textpage program is a vb.net program that checks for new patients that come in through any number of referring web sites. The program text pages the admitting physician with the new patient information prompting them to synchronize their database so that they can see or assign the patient (in an alternative system, the system can also be automatically synchronized using a wireless system connected to the physicians EMR tool). It also scans for any indication that the system isn't performing properly (i.e. the hospital has stopped sending interface data or the lab processor has stopped processing it) and if it sees that condition, it text pages the IT person on call.

Autofax Service

In one embodiment, the Autofax service is a vb.net program that checks for any orders that a physician might want to autofax to the floor (e.g., a new patient that they might not have time to see, but they still want to provide some basic admitting orders). Using the physician's EMR tool, they create the order set and synchronize their database. The system knows where to fax the orders based on the patient's room number. This system can be further enhanced to automatically fax H&Ps and discharge summaries to primary care physicians or admitting physicians in the case of an H&P done at night.

Voice Check-In IVR

In one embodiment, the IVR asks the caller to enter the patient's medical record number, and records the caller's check-in. The check-in, along with the patient's medical record number is inserted into the admission queue. The check-in is also copied to the admitting physician's voicemail box, where the Persistent Pager service will automatically call the admitting physician's cell phone and play the check-in back to the admitting physician.

H&P Check-In IVR

In one embodiment, this IVR application is very similar to the voice check-in IVR, except that it asks for the patient's social security number instead of medical record number (because the patient has not been assigned a medical record number yet). This application is preferably used by physicians who will be requesting night service to do their patient's H&P. These are typically transfers coming in from outlying hospitals for care that is not provided at the outlying hospital. Once the voice H&P check-in is left, they are generally hidden from the physician EMR tools (i.e., not viewable on the admission queue). They are left hidden because the patient has not yet arrived at the hospital. Once the patient arrives at the hospital the unit clerk at the hospital is trained to go to the group's designated website and enter the patient's identification data (e.g., medical record number) and other relevant patient data. The system, via the QuickAdmit service associates the H&P check-in with the unit clerk's check-in and updates the admission queue with the patient's check-in information which may then be viewed by the physicians through the EMR tools.

Phone Routing Application

In one embodiment, this IVR application listens for calls about patients under the group's care. It asks the caller to enter the patient's birthday or first four letters of the patient's last name. It then looks to see if there are any matches. If matches are found, it routes the caller to the cell phone and office phone of the assigned doctor (it also checks the call schedule and forwards to the covering doctor if the assigned doctor isn't currently accepting calls). If the doctor does not answer their cell phone, the caller is placed into the doctor's voice mail. If there are multiple matches to the user's input, it plays back the spelling of the first name of the matches and asks the caller to choose which patient is the one they are calling about. If the caller presses # indicating they want to admit a patient, or that their patient wasn't found in the system, the call is handed off to the admit line round robin IVR application.

Admit Line Round Robin IVR

In one embodiment, this IVR application handles any calls where the caller indicates that they want to speak with the admitting physician or any routing calls where the user's input did not match to a patient in the system. The program looks at all doctors currently accepting calls and then routes the call to the doctor with the longest idle time (i.e. the one who has gone the longest without getting any kind of call from the system).

PersistentPager Service

In one embodiment, the service is a vb.net program that scans the physicians' voicemail boxes for any unheard messages. If the unheard message is tagged as a voice check-in, it calls the doctor immediately. If the message is flagged as coming in through the routing application, it waits 10 minutes to call the doctor (it doesn't call them immediately because it just got done trying to push the call through to their cell phone). It ignores any messages left from callers calling the doctor's office phone directly, since these calls are of a business nature, not patient care nature. It then attempts to call the doctor's cell phone every 10 minutes until they listen to the voice mails. Once connected, the doctor has several choices when listening to the voice mail. First, the voice mail is played back at an accelerated, yet still understandable rate. The doctor can choose to slow the message down, rewind, fast forward, pause, delete, and skip to the next message or move to the previous message.

Voicemail Playback

In case the doctor wants to check their voicemail before waiting for the 10 minute period to elapse, they can call into the voicemail playback IVR. If they call from their cell phone, the system recognizes their caller id and automatically logs them in, if not, it asks them for their user ID and password and then gives them access to their voicemail box.

External Call Router

In one embodiment, this IVR application is designed for physician practices that do not have their patient census in an electronic format. It presents the caller with the list of doctors who are rounding that day according to a schedule that they input into the database. It then routes the caller directly to that doctor's cell phone. At night, when one doctor is taking calls, it routes the caller directly to that doctor, rather than presenting them with a list of doctors. By assigning a dialed number (e.g., DID or DNIS) to each practice using the system, this application can host an unlimited number of physician practices.

EMR Tool

This program preferably runs on a laptop in conjunction with a local SQL Server database. It supports physician rounding, including viewing the admission queue, assigning patients to physicians, showing labs from the hospital interface, generating H&Ps, consult notes, progress notes and discharge summaries. It also allows the physician to record any procedures or critical care time. This information is then picked up by the back office application to generate bills and provide credentialing reports. It is preferred that the laptops also run a local version of SQL Server, which allows them to keep an "offline" copy of their data.

BackOffice Software

In one embodiment, the back office software is programmed to automatically generate claims for electronic submission. It also posts payments electronically, as well as manually, and stores images of Explanation of Benefits from insurance companies. It also prompts the user to research the address and phone and fax numbers of any new physician that needs a discharge summary. It also generates payroll reports and automatically interfaces this information into a payroll service. A collections module helps the company ensure that it is collecting every dollar it can for services rendered.

Consult Web Site

In one embodiment, this web site allows unit clerks to notify the group of new consults or psychiatric H&Ps. The unit clerks enter the patient's medical record number and the reason for the consult or H&P and their phone number. The site then places the information in the admission queue as previously discussed.

Scheduling Application

In one embodiment, the scheduling program allows the user to create a rounding schedule using a drag and drop interface. A similar program is used to create the schedule for the external practice phone routing application. The program lists the type and number of shifts required for each day (i.e. day, critical care and H&P shifts). It also lists the tally of each shift type per physician. This program may be enhanced with algorithms to automatically generate and adjust the rounding schedule. It will also include a web site allowing physicians to submit scheduling requests.

Field Autosynch Service

In one embodiment, this service will run on the physician laptops and automatically initiate a database synchronization job anytime the laptop is brought out of standby and within range of a wireless Internet connection. It will also prevent the laptop from entering standby when the lid is closed if a synchronization job is taking place.

Patient Autoassignment

In one embodiment, a patient autoassignment program is a vb.net service that automatically assigns new patients during the day based on where the rounding physicians have been, where they are going, what their next day's schedule looks like, and what their rounding capacity is, as determined by some system factors and what the physician chooses as how many patients they want to see. It will also assign patients in the morning as part of rounds preparation based on a variety of factors including room location, physician capacity, visit complexity, and continuity of care. Accordingly, for example, new patients received through the voice check-in procedure can be automatically assigned via this program. These assignments will be stored in the system and synchronized to the physician's EMR tools as previously discussed.

Hospital Past Medical History Application

In one embodiment, this application may be used by the hospital to document the patient's past medical history and home medications. It will then interface this information to the hospital's database repository as well as our web service, which will allow the group using the system of the present invention to automatically enter this information into the system instead of having a physician manually type it in.

Shift Trading System

In one embodiment, the system will be configured with a program that allows physicians to buy and sell different shift types, allowing each physician in the group to specify their individual shift preferences. If a particular physician does not want to work weekends, the physician can put those shifts up for sale hoping that another physician will buy those shifts or trade for other shifts.

In another embodiment, the invention is comprised of a "family check-in" system where the doctor can leave daily check-ins through an electronic medical record and have family members retrieve the check-ins via a PIN that is assigned to the patient during the admission process. This will eliminate the need for doctors and family members to play phone tag. For example, the doctor can enter a status report for a patient via the EMR tool (having voice capability). The message is recorded along with patient identification data, such as the medical record number. The message and data is preferably saved in a SQL database in a family update table. Subsequently, a family member can call in and be routed to an IVR script which asks the family member to input a PIN number and patient identification data to obtain access to the physicians status report regarding the patient.

It is thought that the advantages of the present invention will be apparent from the description of the drawings and the preferred embodiments contained herein. It will be appreciated that after reading this specification those skilled in the art will arrive at various modifications to the invention described herein and these modifications are anticipated to fall within the scope of the present invention and the claims contained herein.

What is claimed is:

1. A system for admitting patients into a hospital for in-patient care, comprising:

a computer processing system including a memory device, the memory device including a database configured to store information, the information including patient information stored in a database admissions queue, a duty schedule for each of one or more admitting physicians and contact information for each of the one or more admitting physicians;

wherein the duty schedule for the one or more admitting physicians includes the names of each of the one or more admitting physicians on-staff at the hospital, and the dates and time that each of the one or more admitting physicians is on-duty; and wherein the contact information for each of the one or more admitting physicians includes a telephone number for a communication device of each of the one or more admitting physicians;

a telephone server including an integrated voice response (IVR) system programmed with one or more software routines executing on the telephone server and configured to:

receive a telephone call, via a telephone device, from one or more referring medical practitioners;

answer the telephone call;

receive the patient information for a particular patient waiting to be admitted into the hospital for in-patient care including:

identification information for the particular patient, entered via the telephone device, and a voice message, transmitted via the telephone device, that includes further health information relating to the particular patient;

store the particular patient's identification information in the database admissions queue and record and store the voice message in the database admissions queue as a voice recording;

store a time that the patient information for the particular patient was stored in the database admissions queue;

the telephone server is further configured to:

place a telephone call to the communication device of an on-duty admitting physician at the hospital and to play the voice recording for the particular patient if the on-duty admitting physician answers the call; and the computer processing system programmed with one or more software routines executing on the computer processing system and configured to:

generate a graphical view of the database admission queue configured to be displayed on a mobile computing platform of the one or more admitting physicians;

receive a request for access to the patient information stored in the database admission queue from the mobile computing platform of one of the one or more admitting physicians;

transmit, in response to the request, the patient information to the requesting mobile computing platform, the patient information including the patient identification information, the time the patient information was stored in the database, and a link to the voice recording relating to each patient, and delete the patient information for the particular patient from the database admissions queue when the particular patient has been admitted into the hospital for in-patient care.

2. A system according to claim 1, wherein the call to the communication device of the on-duty admitting physician is made over a mobile phone network.

3. A system according to claim 1, wherein the identification information is a medical record number.

4. A system according to claim 1, wherein the identification information is a social security number.

5. A system according to claim 1, wherein the health information includes past medical history, any allergies, and reason for hospitalization.

6. A system according to claim 1, wherein the telephone server is programmed with one or more software routines executing on the telephone server and configured to play the voice message at a faster rate than recorded.

7. A system according to claim 1, wherein the telephone server is further programmed with one or more software routines executing on the telephone server and configured to re-call the communication device of the on-duty admitting physician after a predetermined period of time if the on-duty admitting physician does not answer the telephone call.

8. A system according to claim 1, wherein the computer processing system is further programmed with one or more software routines executing on the computer processing system and configured to:

access a hospital database having additional patient data; and append the additional patient data to the database admissions queue.

9. A system according to claim 1, wherein the telephone server is further programmed with one or more software routines executing on the telephone server and configured to:

track the idle time of each on-duty admitting physician; and route the call to the on-duty admitting physician with the longest idle time.

* * * * *